US00PP31946P2

(12) United States Plant Patent
Koot

(10) Patent No.: US PP31,946 P2
(45) Date of Patent: Jul. 7, 2020

(54) POINSETTIA PLANT NAMED 'DUEPOWHIWON'

(50) Latin Name: ***Euphorbia pulcherrima* Willd.**
Varietal Denomination: Duepowhiwon

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,412

(22) Filed: Apr. 9, 2019

(51) Int. Cl.
*A01H 5/02* (2018.01)
*A01H 6/38* (2018.01)

(52) U.S. Cl.
USPC ..... Plt./305

(58) Field of Classification Search
USPC ..... Plt./302, 303, 305
See application file for complete search history.

*Primary Examiner* — Susan McCormick Ewoldt
(74) *Attorney, Agent, or Firm* — C. A. Whealy

(57) ABSTRACT

A new and distinct cultivar of *Poinsettia* plant named 'Duepowhiwon', characterized by its upright to slightly outwardly spreading and uniformly mounding plant habit; moderately vigorous growth habit; strong lateral branches; relatively early flowering habit; inflorescences with large pale yellow-colored flower bracts; and excellent post-production longevity.

1 Drawing Sheet

Botanical designation: *Euphorbia pulcherrima* Willd.
Cultivar denomination: 'DUEPOWHIWON'.

BACKGROUND OF THE INVENTION

The present invention relates to a new and distinct cultivar of *Poinsettia* plant, botanically known as *Euphorbia pulcherrima* Willd., and hereinafter referred to by the name 'Duepowhiwon'.

The new *Poinsettia* plant is a product of a planned breeding program conducted by the Inventor in Rheinberg, Germany. The objective of the breeding program is to create moderately vigorous *Poinsettia* plants with strong lateral branches, upright plant habit and attractive flower bract coloration.

The new *Poinsettia* plant originated from a cross-pollination made by the Inventor in July, 2013 in Rheinberg, Germany of a proprietary selection of *Euphorbia pulcherrima* Willd. identified as code number EE04-000817-001, not patented, as the female, or seed, parent with a proprietary selection of *Euphorbia pulcherrima* Willd. identified as code number EE09-002443-001, not patented, as the male, or pollen, parent. The new *Poinsettia* plant was discovered and selected by the Inventor as a flowering plant from within the progeny of the stated cross-pollination in a controlled greenhouse environment in Rheinberg, Germany in December, 2017.

Asexual reproduction of the new *Poinsettia* plant by terminal vegetative cuttings in a controlled greenhouse environment in Rheinberg, Germany since January, 2018 has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Duepowhiwon'. These characteristics in combination distinguish 'Duepowhiwon' as a new and distinct *Poinsettia* plant:

1. Upright to slightly outwardly spreading and uniformly mounding plant habit.
2. Moderately vigorous growth habit.
3. Strong lateral branches.
4. Relatively early flowering habit.
5. Inflorescences with large pale yellow-colored flower bracts.
6. Excellent post-production longevity.

Plants of the new *Poinsettia* differ primarily from plants of the female parent selection in flower bract color as plants of the new *Poinsettia* have pale yellow-colored flower bracts and plants of the female parent selection have red-colored flower bracts.

Plants of the new *Poinsettia* differ primarily from plants of the male parent selection in leaf color as plants of the new *Poinsettia* have darker green-colored leaves than plants of the male parent selection. In addition, the lower surface of the flower bracts of plants of the new *Poinsettia* are slightly more rugose than the lower surface of the flower bracts of plants of the male parent selection.

Plants of the new *Poinsettia* can be compared to plants of *Euphorbia pulcherrima* Willd. 'Dueinfinitywi', disclosed in U.S. Plant Pat. No. 19,995. In side-by-side comparisons, plants of the new *Poinsettia* differ primarily from plants of 'Dueinfinitywi' in the following characteristics:

1. Plants of the new *Poinsettia* are more upright than and not as outwardly spreading as plants of 'Dueinfinitywi'.
2. Plants of the new *Poinsettia* have longer leaves than plants of 'Dueinfinitywi'.

3. Flower bracts of plants of the new *Poinsettia* are longer and broader than flower bracts of plants of 'Dueinfinitywi'.

BRIEF DESCRIPTION OF THE PHOTOGRAPH

The accompanying photograph illustrates the overall appearance of the new *Poinsettia* plant showing the colors as true as it is reasonably possible to obtain in colored reproductions of this type. Colors in the photograph may differ slightly from the color values cited in the detailed botanical description which accurately describe the colors of the new *Poinsettia* plant. The photograph comprises a side perspective view of a typical flowering plant of 'Duepowhiwon' grown in a container.

DETAILED BOTANICAL DESCRIPTION

The aforementioned photograph and following observations and measurements describe plants grown in Rheinberg, Germany during the summer and autumn in a glass-covered greenhouse and under cultural practices typical of commercial *Poinsettia* production. During the production of the plants, day and night temperatures averaged 18° C. and light levels averaged 4,500 lux. Single plants were grown in 13-cm containers and were pinched one time about three weeks after planting the cuttings. Plants were 23 weeks old when the photograph and the detailed description were taken. In the following description, color references are made to Royal Horticultural Society Colour Chart, Fifth Edition, except where general terms of ordinary dictionary significance are used.

Botanical classification: *Euphorbia pulcherrima* Willd. 'Duepowhiwon'.

Parentage:

*Female, or seed, parent*.—Proprietary selection of *Euphorbia pulcherrima* Willd. identified as code number EE04-000817-001, not patented.

*Male or pollen parent*.—Proprietary selection of *Euphorbia pulcherrima* Willd. identified as code number EE09-002443-001, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant habit and form*.—Upright to slightly outwardly spreading and uniformly mounding plant habit; moderately vigorous growth habit; inverted triangle in overall plant shape; inflorescences with large flower bracts positioned above the foliar plane.

*Plant height*.—About 25 cm.

*Plant diameter or spread*.—About 35 cm.

*Lateral branch description*.—Quantity: Freely branching habit with about six to seven lateral branches developing after pinching. Length: About 22 cm. Diameter: About 6 mm. Internode length: About 1.2 cm. Strength: Strong. Texture: Smooth, glabrous. Color: Close to 137A.

*Leaf description*.—Arrangement: Alternate, simple. Length: About 11.7 cm. Width: About 7.6 cm. Shape: Ovate. Apex: Apiculate. Base: Obtuse. Margin: Dentate. Texture, upper surface: Glabrous; smooth. Texture, lower surface: Glabrous; rugose. Venation pattern: Pinnate. Color: Developing leaves, upper surface: Close to 135A. Developing leaves, lower surface: Close to 138A. Fully expanded leaves, upper surface: Close to 139A; venation, close to 146A. Fully expanded leaves, lower surface: Close to 137B; venation, close to 146B to 146C. Petioles: Length: About 5 cm. Diameter: About 3 mm. Texture, upper and lower surfaces: Smooth, glabrous. Color, upper and lower surfaces: Close to 144A.

Inflorescence description:

*Inflorescence type and habit*.—Inflorescences are compound corymbs of cyathia with flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; relatively early flowering habit, response time is about eight weeks.

*Post-production longevity*.—Excellent post-production longevity; plants of the new *Poinsettia* maintain good substance and bract color for about twelve weeks under interior conditions.

*Inflorescence size*.—Diameter: About 33 cm. Height (depth): About 3 cm.

*Flower bracts*.—Quantity per inflorescence: About 15. Length: About 17 cm. Width: About 11.7 cm. Shape: Ovate. Apex: Apiculate. Base: Obtuse. Margin: Dentate. Aspect: Mostly flat. Texture, upper surface: Glabrous; smooth. Texture, lower surface: Glabrous; rugose. Venation pattern: Pinnate. Color: Developing bracts, upper and lower surfaces: Close to 18D. Transitional bracts, upper and lower surfaces: Close to 18C. Fully developed bracts, upper and lower surfaces: Close to 8D; venation, close to 8D; color does not change with development. Bract petioles: Length: About 1.6 cm. Diameter: About 2 mm. Texture, upper and lower surfaces: Smooth, glabrous. Color, upper and lower surfaces: Close to 144C.

*Cyathia*.—Quantity per corymb: About 15. Length: About 8 mm. Width: About 5 mm. Shape: Ovoid. Texture, inner and outer surfaces: Smooth, glabrous. Color: When developing, inner surface: Close to 143C. When developing, outer surface: Close to 143B. Fully developed, inner surface: Close to 143B. Fully developed, outer surface: Close to 143B to 143C. Nectaries: Quantity per cyathium: Typically one. Length: About 4 mm. Diameter: About 1 mm. Shape: Ovoid. Texture, inner and outer surfaces: Smooth, glabrous. Color: When developing and fully developed, inner surface: Close to 17A. When developing and fully developed, outer surface: Close to 17C.

*Peduncles*.—Length: About 4 mm. Diameter: About 2 mm. Strength: Strong. Texture: Smooth, glabrous. Color: Close to 143C.

*Reproductive organs*.—Stamens: Quantity per cyathium: About 25. Filament length: About 5 mm. Filament color: Close to 49C. Anther shape: Oval. Anther length: About 0.5 mm. Anther color: Close to 9B. Amount of pollen: Abundant. Pollen color: Close to 14A. Pistils: Quantity per cyathium: One. Pistil length: About 1 cm. Style length: About 2 mm. Style color: Close to 144B. Stigma shape: Crested. Stigma color: Close to 46B. Ovary color: Close to 144A. Seeds and fruits: To date, seed and fruit production have not been observed on plants of the new *Poinsettia*.

Pathogen & pest resistance: To date, plants of the new *Poinsettia* have not been shown to be resistant to pathogens and pests common to *Poinsettia* plants.

Temperature tolerance: Plants of the new *Poinsettia* have been observed to tolerate temperatures ranging from about 12° C. to about 40° C.

It is claimed:

1. A new and distinct *Poinsettia* plant named 'Duepowhiwon' as illustrated and described.

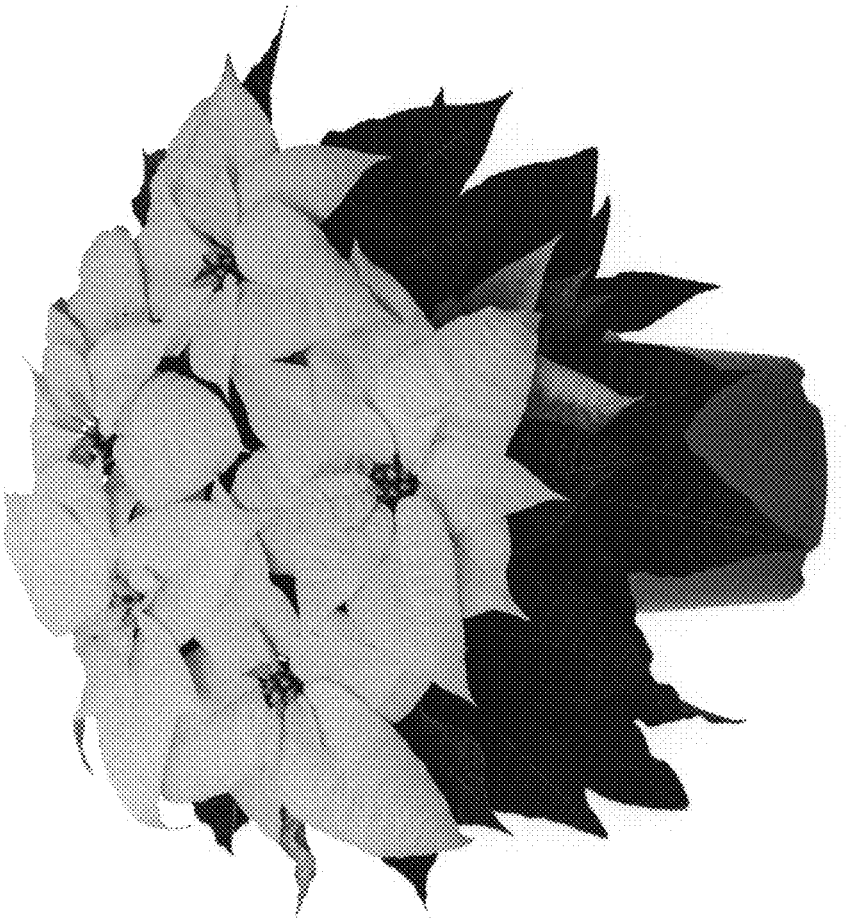

* * * * *